US012648689B1

(12) United States Patent
Hester et al.

(10) Patent No.: US 12,648,689 B1
(45) Date of Patent: Jun. 9, 2026

(54) WAVEFRONT PHASE IMAGER FOR OPTICAL COMMUNICATIONS

(71) Applicants: C. Anthony Hester, Huntsville, AL (US); Charles F. Hester, Huntsville, AL (US)

(72) Inventors: C. Anthony Hester, Huntsville, AL (US); Charles F. Hester, Huntsville, AL (US)

( * ) Notice: Subject to any disclaimer, the term of this patent is extended or adjusted under 35 U.S.C. 154(b) by 303 days.

(21) Appl. No.: 18/441,752

(22) Filed: Feb. 14, 2024

Related U.S. Application Data

(60) Provisional application No. 63/484,895, filed on Feb. 14, 2023.

(51) Int. Cl.
*A61B 3/10* (2006.01)
*A61B 3/00* (2006.01)
(52) U.S. Cl.
CPC .......... *A61B 3/1015* (2013.01); *A61B 3/0025* (2013.01)
(58) Field of Classification Search
CPC ....... A61B 3/102; A61B 3/1025; A61B 3/103; A61B 3/1015; A61B 3/0025

USPC .......................................................... 351/205
See application file for complete search history.

(56) References Cited

U.S. PATENT DOCUMENTS 11,067,477 B2 * 7/2021 Suzuki ................. G01M 11/005

* cited by examiner

*Primary Examiner* — Henry Duong
(74) *Attorney, Agent, or Firm* — Maynard Nexsen PC; Brian T. Sattizahn

(57) ABSTRACT

A wavefront phase imager is provided for optical communications. The wavefront imager can be an optical system that can measure and/or correct for the distortions in a monochromatic wavefront. A measurement configuration of the wavefront imager can operate in the spatial Fourier space and use interference of the incoming light to the measure the phase shift or distortion of the monochromatic wavefront. A correction configuration of the wavefront imager can also operate in the spatial Fourier space and make corresponding adjustments to the monochromatic wavefront such that the resultant wavefront from the wavefront imager has a constant phase.

20 Claims, 4 Drawing Sheets

WAVEFRONT PHASE IMAGER FOR OPTICAL COMMUNICATIONS

CROSS-REFERENCE TO RELATED APPLICATIONS

This application claims the benefit of U.S. Provisional Application No. 63/484,895, entitled "Interferometric Fourier Wave-Front Phase Imager and Corrector," filed Feb. 14, 2023, which application is hereby incorporated by reference in its entirety.

BACKGROUND

The present application generally relates to a wavefront phase imager for optical communications. More specifically, the present application is directed to a wavefront phase imager with an interferometric architecture operating in the spatial Fourier space. Optical communications (e.g., communications using a light or laser) can be preferred over radio frequency (RF) communications due to the longer transmission distances and the increased data capacity provided by optical communications. However, one drawback to using optical communications is the susceptibility of optical communications to distortion during transmission.

For example, when a monochromatic (or single wavelength) plane wave (i.e., the light or laser of optical communications) travels through a medium (e.g., the atmosphere), non-uniformities in the index of refraction of the medium (such as those caused by variations in the density of the medium) can lead to a distortion of the wavefront of the plane wave. As shown in FIG. 1, an unperturbed wavefront 12 of a plane wave passes through a inhomogeneous medium 14 (e.g., the atmosphere) which results in a perturbed wavefront 16.

In order to compensate for the distortion caused by the medium, a measurement of the phase shift (or distortion) of the wavefront is needed, which can be defined in the function F. One way to determine F is to let P (see FIG. 1) represent a reference plane parallel to the unperturbed wavefront 12 and then determine the vertical distance of the perturbed wavefront 16 at x relative to P to obtain F(x). Many applications require knowledge of the distortion or phase shift of a wavefront (i.e., the function F) for proper operation. For example, astronomers measure F to correct for atmospheric distortions.

One type of wavefront sensor that can be used to determine the distortion or phase shift of the wavefront (or the function F) is a Shack-Hartmann architecture. As shown in FIG. 2, a Shack-Hartmann wavefront sensor 20 can have a lenslet array 22 that focuses the light from an incoming wavefront 24 to a series of spots 28 on a two dimensional detector array 26. As dictated by geometrical optics, the gradient of F relates to the position of the spot ($\Delta$x) relative to the optical axis of the lenslet via the equation $\nabla F = \Delta x/f$, where f denotes the focal length of the lenslet. However, the Shack-Hartmann wavefront sensor has several drawbacks such as: the diffraction of the lenslets limit the light causing uncertainty in the position of the spot; the structure of the lenslet array absorbs a percentage of the photons, impairing the efficiency of the device; and the possibility of adjacent spots overlapping, making it difficult or impossible to determine the position of the affected spots. In addition, with the Shack-Hartmann wavefront sensor there is a trade-off between accuracy and dynamic range. If you want more accuracy, you need more spot motion per small changes in the wavefront. The extra sensitivity causes more overlaps, and, in the worst case, the complete inability to measure F at certain points. To address the drawbacks of the Shack-Hartmann wavefront sensor, significant post-processing may be needed to reconstruct F, which can generate heat and reduce the sample rate of the wavefront sensor. Therefore, what is needed is a more accurate and efficient way to detect the phase shift of a wavefront.

SUMMARY

The present application generally pertains to a wavefront imager for optical communications that has an interferometric architecture (i.e., using the interference of light to measure phase) operating in the spatial Fourier space (i.e., rearranging the photons to facilitate the measurement of the phase). The wavefront imager can be an optical system that can measure and/or correct for the distortions in a monochromatic wavefront, without utilizing a reference beam, by analyzing and acting on the spatial two-dimensional (2D) Fourier transform of the wavefront In some embodiments, the wavefront imager can include Fourier optics to compute the 2D Fourier spatial transform of the incoming wavefront. The wavefront imager can also include a correcting device to provide for alignment and removal of distortions from the wavefront. In other embodiments, the wavefront image has a DC pick-off device to isolate the DC component of the 2D Fourier spatial transform of the wavefront from the non-DC components of the 2D Fourier spatial transform of the wavefront. The wavefront imager can also include a path length adjustor to adjust the phase between the plane wave version of the DC component and the non-DC components of the wavefront. The wavefront imager can further include imaging optics to focus the non-DC components of the wavefront on the detector and, optionally, take the inverse Fourier transform of the non-DC components. In addition, the wavefront imager can include combining optics for interfering the DC component of the wavefront, and the non-DC components of the wavefront. The wavefront imager includes a detector and post processor for imaging the non-DC components. If the wavefront imager includes the path length adjustor, then the detector images the interference pattern of the plane wave version of the DC component with the non-DC components. The post processor (or post processing circuitry) can implement a phase lock loop at each pixel to measure the time during the path length adjuster movement at which maximum interference occurs and thereby determine when the DC component and the non-DC components are in phase.

An advantage of the present application is that the imager can operate at high speeds with minimal post processing.

Another advantage of the present application is that operating the imager in the Fourier space ensures that energy concentrates around the optical axis and provides increased sensitivity.

A further advantage of the present application is that the imager can measure the wavefront down to the size (or wavelength) of the photons.

Still another advantage of the present application is that the imager can process large gradients in the function F, thereby reducing ambiguities caused by branch points (or large changes in phase).

Other features and advantages of the present application will be apparent from the following more detailed description of the identified embodiments, taken in conjunction with the accompanying drawings which show, by way of example, the principles of the application.

BRIEF DESCRIPTION OF THE DRAWINGS

Wherever possible, the same reference numbers are used throughout the drawings to refer to the same or like parts.

DETAILED DESCRIPTION

Figure 1:
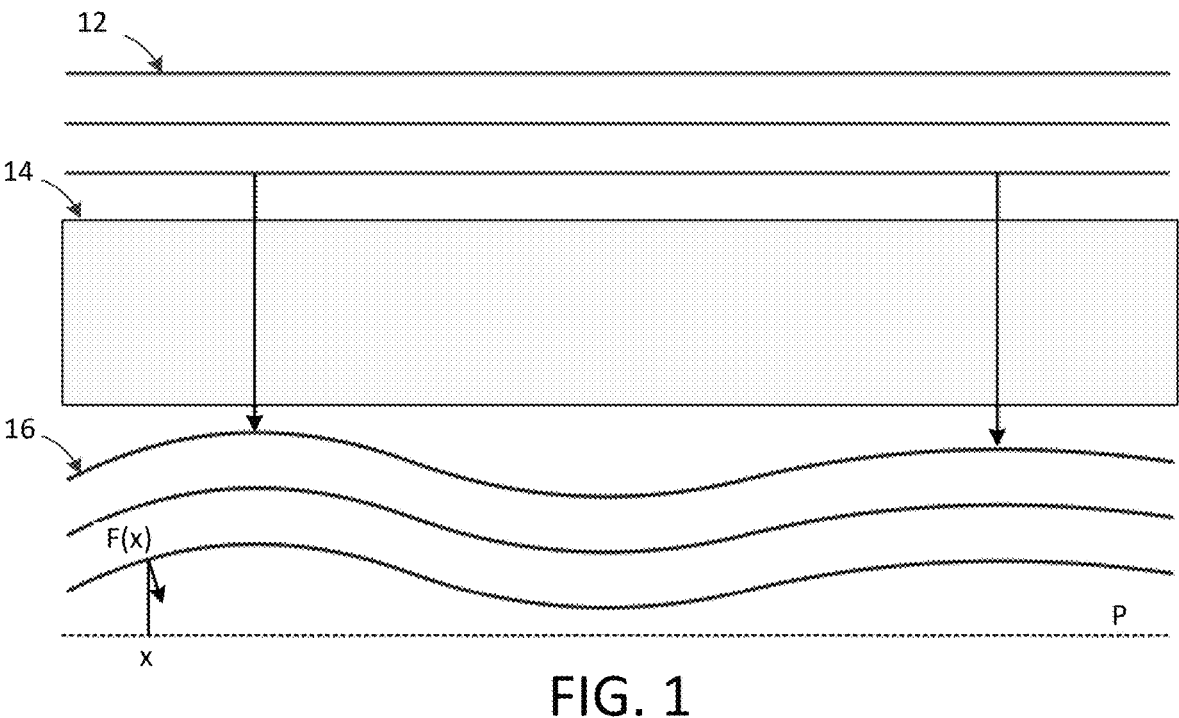
FIG. 1 is a schematic diagram showing a perturbation of a wavefront and the measurement of the distortion of the perturbed wavefront.
Figure 2:
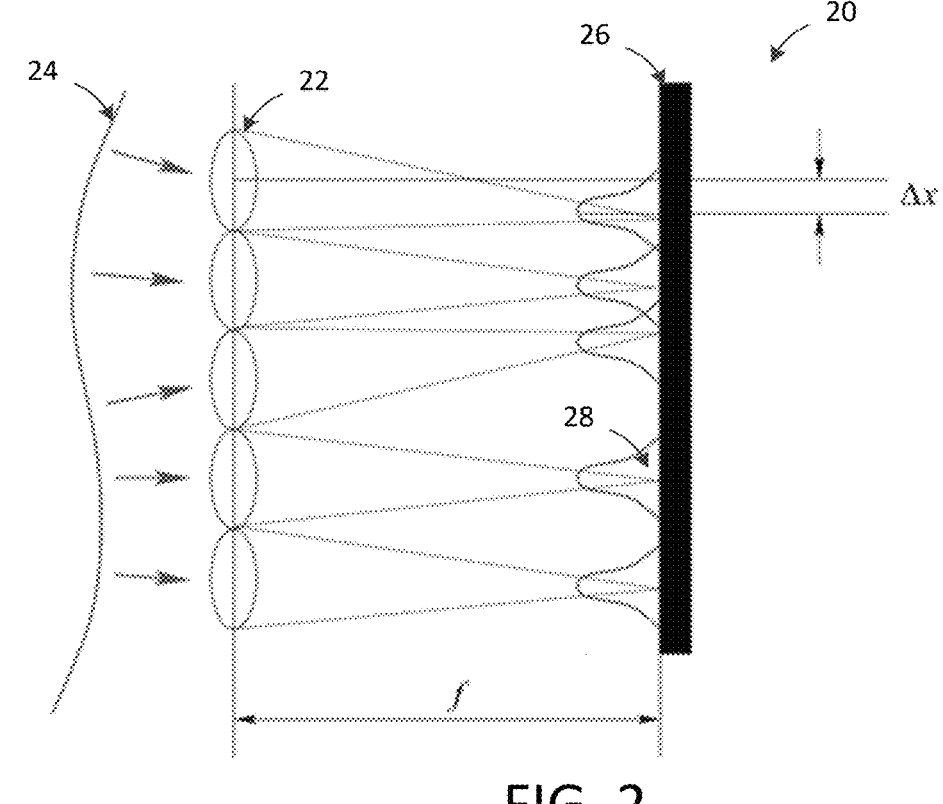
FIG. 2 is a schematic diagram of a prior art wavefront sensor.
Figure 3:
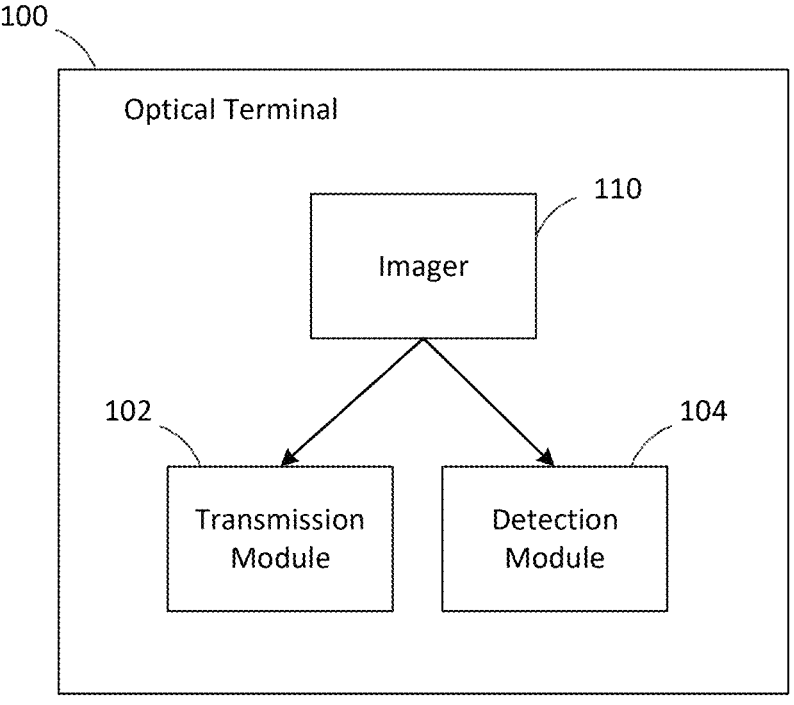
FIG. 3 is a block diagram of an embodiment of an optical terminal.

FIG. 3 shows an embodiment of an optical terminal that can be used for optical communications, such as laser communications, in one embodiment. The optical terminal 100 can be used to communicate information or data using a beam of light from a laser. The laser (Light Amplification by Stimulated Emission of Radiation) is a device that stimulates atoms or molecules to emit light at particular wavelengths, which is then amplified to produce a narrow beam of light. When used for communication, the light from the laser can be in the near-infrared range, having a wavelength of around 900 to around 1600 nanometers. However, in other embodiments, the wavelength of the light from the laser can be longer than 1600 nanometers or shorter than 900 nanometers (e.g., light in in the visible, infrared, or ultraviolet regions). In another embodiment, the optical terminal 100 can be used for higher power output applications from the laser (i.e., having a power output of at least 1 kilowatt).

The optical terminal 100 can include a transmission module 102 that can be used to send or transmit data or information using a laser and a detection (or receiver) module 104 that can be used to receive data or information transmitted by a laser. The optical terminal 100 can also include an imager 110 that can measure and/or correct for the distortions in a monochromatic wavefront (e.g., the beam of light from the laser). The imager 110 can be used to improve the performance of one or both of the transmission module 102 or the detection module 104 and may be incorporated into one or both of the transmission module 102 and the detection module 104 in some embodiments. For example, the correction of distortions in the wavefront by the imager 110 (or the providing of information about the distortions in the waverfront) can improve the accuracy and reliability of information from the detection module 104. Similarly, when the transmission module 102 is preparing to transmit information, having information regarding about the possible distortion of the wavefront can be used to enhance the transmission parameters from the transmission module 102 such that the wavefront received by a subsequent detection module 104 located elsewhere has improved accuracy and reliability. While not specifically shown in FIG. 3, the optical terminal 100, the transmission module 102 and/or the detection module 104 may include any appropriate hardware (e.g., processors, memory devices, sensors, refractive and/or reflective optical components, or other appropriate circuitry) and software needed for proper operation.

Figure 4:
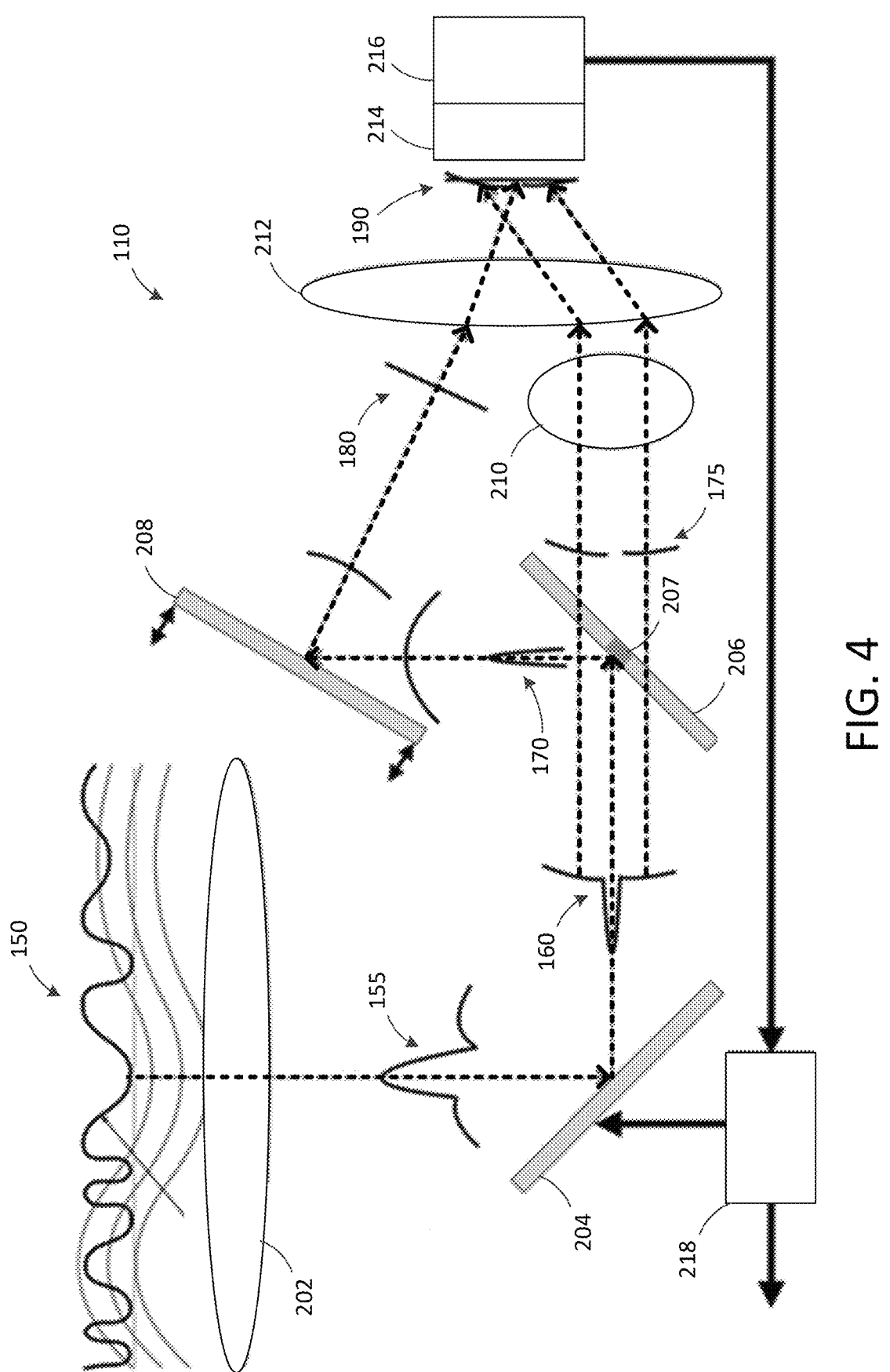
FIG. 4 is a block diagram of an embodiment of the imager from the optical terminal of FIG. 3 that measures distortion in a wavefront.

FIG. 4 shows an embodiment of the imager 110 from the optical terminal 100 that can be used to quantify or measure the phase shift or distortion (i.e., the function F) of an incoming wavefront. The imager 110 can include a Fourier optical system 202 that receives an incoming perturbed wavefront 150 as an input. The Fourier optical system 202 can include one or more optical elements to compute the 2-dimensional spatial Fourier transform of the incoming wavefront 150. The Fourier optical system 202 can include lenses (or refractive elements) and/or mirrors (or reflective elements) to produce the Fourier version of the perturbed wavefront 155. In another embodiment, the Fourier optical system 202 can include a notch filter that operates to permit a preselected frequency range from the incoming wavefront 150 to pass through the Fourier optical system 202. The notch filter can be configured as a coating on one or more lenses of the Fourier optical system 202 or the notch filter can be a separate "changeable" filter that can be modified to adjust the preselected frequency range that is permitted to pass through the Fourier optical system 202.

The Fourier version of the perturbed wavefront 155 is then provided to a correcting or correction device 204 to align and/or remove distortions from the Fourier version of the perturbed wavefront 155 into a corrected Fourier version of the perturbed wavefront 160. In one embodiment, the correcting device 204 can be an optomechanical device, such as an electronically steerable mirror. However, other suitable devices may be used in other embodiments. The corrected Fourier version of the perturbed wavefront 160 is then provided to a DC pick-off or separation device 206. The DC pick-off device 206 can include a reflective component 207 to separate the DC component from the corrected Fourier version of the perturbed wavefront 160. The DC pick-off device 206 can then reflect the DC component 170 of the corrected Fourier version of the perturbed wavefront 160 toward the path length adjustor 208, while the remainder of the corrected Fourier version of the perturbed wavefront 160 (i.e., the non-DC components 175) pass through the DC pick-off device 206 to the imaging optics 210. In one embodiment, the DC pick-off device 206 can be a transparent material (e.g., clear glass) to permit the non-DC components 175 to pass through the DC pick-off device 206. The reflective component 207 of the DC pick-off device 206 can be a metallic component (e.g., a small circle (or other suitable shape) of metal) deposited or located at the anticipated (or expected) location of the DC component of the corrected Fourier version of the perturbed wavefront 160 to reflect the DC component 170 to the path length adjustor 208.

The DC component 170 is provided to a path length adjustor 208 that reflects the DC component 170 to the combining optics 212. The path length adjustor 208 can be movable either toward or away from the detector 214 (and the combining optics 212) to increase or decrease the path length travelled by the DC component 170. In one embodiment, the path length adjustor 208 can be cycled across the full wavelength of the light of the incoming wavefront 150. In addition, the path length adjustor 208 ensures that the DC component 170 travels a sufficient distance to be transformed into a plane wave 180 by the time the DC component 170 arrives at the combining optics 212 and/or detector 214. In one embodiment, the path length adjustor 208 can be a piezo-electric actuated mirror that may oscillate to adjust the path length at a pre-determined frequency, or as controlled by the controller 218. However, other suitable devices (e.g., a lens or refractive element) may be used in other embodiments. If a refractive device is used in the path length adjustor 208, the path length needed for transformation of the DC component 170 into a plane wave may be reduced.

The non-DC components 175 can be provided to imaging optics 210. The imaging optics 210 can be used to ensure that the non-DC components 175 are focused on the detector 214. In another embodiment, the imaging optics 210 can be used to compute the inverse Fourier transform of the non-DC components 175 to detect in the image space in contrast with detection in the Fourier space when no inverse Fourier transform is applied. In one embodiment, the imaging optics 210 can include one or more of a lens (or refractive element) and/or a mirror (or reflective element). However, other suitable devices may be used in other embodiments.

The combining optics 212 can combine the plane wave version of the DC component 180 from the path length adjustor 208 with the imaged non-DC components from the imaging optics 210 to create an interference pattern 190. Depending on the particular phase of the plane wave of the DC component 180, which is dependent on the position of the path length adjustor 208, constructive and/or destructive interference is generated in the interference pattern 190. In one embodiment, the combining optics 210 can include one or more of a lens (or refractive element) and/or a mirror (or reflective element). However, other suitable devices may be used in other embodiments.

The interference pattern 190 from the combining optics 212 can then be detected by the detector 214. The detector 214 can capture an image of the phase from the interference pattern 190, which interference pattern 190 is dependent on the position of the path length adjustor 208 and the corresponding phase of the plane wave of the DC component 180 resulting from the position of the path length adjustor 208. In one embodiment, the detector 214 can be a CMOS image sensor having a two-dimensional pixel array that is responsive to or appropriate for the wavelength of the light. Each pixel in the detector 214 can generate a signal representative of the intensity of the light received by the pixel from the interference pattern 190. In an embodiment, the detector 214 can capture a series of images (or snapshots) that correspond to different positions of the path length adjustor 208 as the path length adjustor 208 is moved to cycle through the full wavelength of the light. The detector 214 can then provide or relay the signals from the two-dimensional array to the post processor (or post processing electronics or circuitry) 216. In one embodiment, the postprocessor 216 can be suitable electrical circuitry or a resonate optical cavity (or laser), which implements a phase-lock loop (or phase locking) for each pixel.

In an embodiment, the imager 110 can determine when the DC component is in phase with the non-DC components by moving the path length adjustor 208 toward or away from the detector 214. The movement of the path length adjustor 208 can change path length of the DC component causing the DC component to interfere with different portions of the non-DC components. When the brightness detected by the detector 214 is at a peak or maximum, the DC component is in phase with the non-DC components. Thus, by taking several measurements from the detector 214 while moving the path length adjustor 208, the controller 218 can determine the path lengths for which the DC component is in phase with the non-DC components and use this phase information to calculate F. In other words, after the path length adjustor 208 implements a preselected number of oscillations, the post processor 216 reads or identifies the position of the path length adjustor 208 that results in a peak (as detected by the detector 214) during the oscillation as determined by the phase-lock loop (or generates or modulates a phased laser image of the interferometric image). The post-processor 216 then passes the positions of the path length adjustor 208 corresponding to the peaks detected by the detector 214 to the controller 218.

The controller 218 receives the data about the non-DC components (e.g., peak information and/or image information), and depending on the application, can output the data to one or more of the transmission module 102, the detection module 104 or other component of the optical terminal 100. The controller 218 may also make additional calculations to determine or utilize F, as needed. In one embodiment, the output from the controller 218 may include an array of numbers, each representing the amount of phase shift of a corresponding portion of the wavefront, in the Fourier space, as measured by a pixel of the detector 214 and the corresponding post processing electronics 216. Arrays of phase shift measurements can follow one another, creating a movie of the evolution of the distortion of the wavefront. In other embodiments, the controller 218 can process the data from the post-processor 216 to issue commands to adjust the position of the correcting device 204 and/or control the movement of the path length adjustor 208. For example, the controller 218 may adjust the position of the correcting device 204 in order to tilt the correcting device 204 such that the DC component of the corrected Fourier version of the perturbed wavefront 160 is directed toward (or centered on) the reflective component 207 of the DC-pick-off device 206. Note that the controller 218 may be implemented in hardware or a combination of hardware and software. As an example, the controller 218 may include at least one processor configured to execute instructions stored in memory to perform the functions ascribed to it herein.

Figure 5:
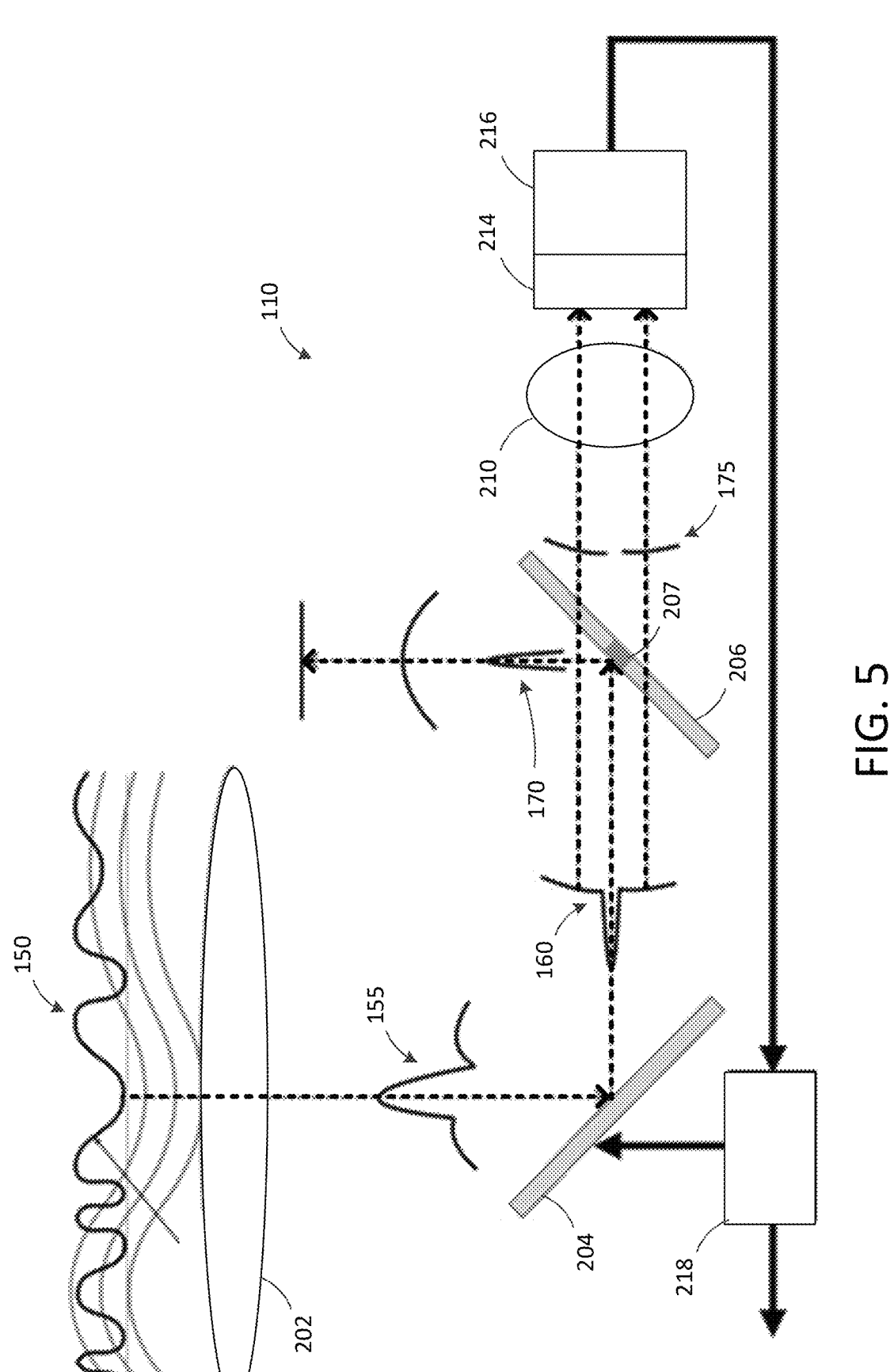
FIG. 5 is a block diagram of an embodiment of the imager from the optical terminal of FIG. 3 that corrects for distortion in a wavefront.

FIG. 5 shows an embodiment of the imager 110 from the optical terminal 100 that can be used to remove or correct for the phase shift or distortion (i.e., the function F) of an incoming wavefront. In other words, one of the outputs of this embodiment of the imager 110 is a corrected version of the wavefront where the new F is a constant function. Similar to the embodiment of the imager 110 from FIG. 4, the imager 110 can include a Fourier optical system 202 that receives an incoming perturbed wavefront 150 as an input. The Fourier optical system 202 can include one or more optical elements to compute the 2-dimensional spatial Fourier transform of the incoming wavefront 150. The Fourier optical system 202 can include lenses (or refractive elements) and/or mirrors (or reflective elements) to produce the Fourier version of the perturbed wavefront 155.

The Fourier version of the perturbed wavefront 155 is then provided to a correcting device 204 to adjust the phase across the Fourier version of the perturbed wavefront 155 to produce a corrected Fourier version of the perturbed wavefront 160. In one embodiment, the correcting device 204 can be an optomechanical device, such as an electronically steerable or deformable mirror. In another embodiment, the correcting device 204 can be a spatial light modulator (SLM). Some examples of SLMs that can be used for the correcting device can be found in the following patents: U.S. Pat. No. 10,209,511 entitled "Spatial Light Moduator for Actuating Microelectromechanical System (MEMS) Structures"; U.S. Pat. No. 10,088,670 entitled "Interference Based Spatial Light Moduator Systems and Methods"; U.S. Pat. No. 10,167,933 entitled "Actuator Systems and Methods"; and U.S. Pat. No. 11,002,347 entitled "Actuator Systems and Methods", with each of the preceding patents being incorporated herein by reference. However, other suitable devices may be used in other embodiments.

The corrected Fourier version of the perturbed wavefront 160 is then provided to a DC pick-off or separation device 206. The DC pick-off device 206 can include a reflective component 207 to separate the DC component from the corrected Fourier version of the perturbed wavefront 160. The DC pick-off device 206 can then reflect the DC component 170 of the corrected Fourier version of the perturbed wavefront 160 toward an output from the imager 110, wherein the output is an optical signal that has been corrected for distortion. The remainder of the corrected Fourier version of the perturbed wavefront 160 (i.e., the non-DC components 175) pass through the DC pick-off device 206 to the imaging optics 210. In one embodiment, the DC pick-off device 206 can be a transparent material (e.g., clear glass) to permit the non-DC components 175 to pass through the DC pick-off device 206. The reflective component 207 of the DC pick-off device 206 can be a metallic component (e.g., a small circle (or other suitable shape) of metal) deposited or located at the anticipated (or expected) location of the DC component of the corrected Fourier version of the perturbed wavefront 160 to reflect the DC component 170 to an output of the imager 110.

The non-DC components 175 can be provided to the imaging optics 210. The imaging optics 210 can be used to ensure that the non-DC components 175 are focused on the detector 214. In another embodiment, the imaging optics 210 can be used to compute the inverse Fourier transform of the non-DC components 175. In one embodiment, the imaging optics 210 can include one or more of a lens (or refractive element) and/or a mirror (or reflective element). However, other suitable devices may be used in other embodiments. The detector 214 can capture images of the non-DC components of the wavefront and pass the data to the controller 218 via the post processor 216.

The controller 218 receives the data about the non-DC components, and depending on the application, can output the data to one or more of the transmission module 102, the detection module 104 or other component of the optical terminal 100. The controller 218 may also make additional calculations to determine and/or utilize F, as needed. In one embodiment, the output from the controller may include an array of numbers, representing the current state of the correcting device 204. For example, if the correcting device 204 is an SLM having an array of vertically adjustable mirrors, then the array of numbers output from the controller represent the position of each mirror in the SLM. In other embodiments, the controller 218 can process the data about the non-DC components from the post-processor 216 to issue commands to the correcting device 204 to make changes to the wavefront such as alignment and phase adjustments. When the correcting device 204 is appropriately positioned so that adjustments by the imager 110 match the distortion in the wavefront, the peak of the DC component becomes very narrow such that a greater amount of energy reflects off the DC pick-off device 206 resulting in a reflected DC component 170 that is substantially free of distortion. At this point, the amount of energy passing through the DC pick-off device 206 and reaching the detector is at minimum, which is detectable by the controller 218 to determine how to position the correcting device 204 to correct for the distortion. In addition, based on the position of the correcting device 204 when distortion is so corrected, the controller 218 can determine the amount of distortion or phase shift that is affecting the input wavefront and, specifically, calculate F. Note that the controller 218 may be implemented in hardware or a combination of hardware and software. As an example, the controller 218 may include at least one processor configured to execute instructions stored in memory to perform the functions ascribed to it herein.

Although the figures herein may show a specific order of method steps, the order of the steps may differ from what is depicted. Also, two or more steps may be performed concurrently or with partial concurrence. Variations in step performance can depend on the software and hardware systems chosen and on designer choice. All such variations are within the scope of the application. Software implementations could be accomplished with standard programming techniques, with rule based logic and other logic to accomplish the various connection steps, processing steps, comparison steps and decision steps.

It should be understood that the identified embodiments are offered by way of example only. Other substitutions, modifications, changes and omissions may be made in the design, operating conditions and arrangement of the embodiments without departing from the scope of the present application. Accordingly, the present application is not limited to a particular embodiment, but extends to various modifications that nevertheless fall within the scope of the application. It should also be understood that the phraseology and terminology employed herein is for the purpose of description only and should not be regarded as limiting.

What is claimed is:

1. An optical system to measure distortion in a monochromatic wavefront, the optical system comprising:
   a first optical system to receive a monochromatic wavefront, the first optical system configured to produce a two-dimensional spatial Fourier transform of the monochromatic wavefront;
   a second optical system to receive the two-dimensional spatial Fourier transform of the monochromatic wavefront, the second optical system configured to separate the two-dimensional spatial Fourier transform of the monochromatic wavefront into a DC component and non-DC components;
   a third optical system to receive the DC component, the third optical system configured to adjust a phase between the DC component and the non-DC components;
   a fourth optical system to receive the DC component from the third optical system and the non-DC components from the second optical system, the fourth optical system configured to interfere the DC component and the non-DC components to produce an interference pattern;
   a detector configured to detect the interference pattern and provide data corresponding to the detected interference pattern; and
   a controller configured to receive the data corresponding to the detected interference pattern and determine an amount of distortion from the received data.

2. The optical system of claim 1, further comprises a fifth optical system to receive the two-dimensional spatial Fourier transform of the monochromatic wavefront, the fifth optical system configured to remove distortions from the two-dimensional spatial Fourier transform of the monochromatic wavefront and align the DC component of the two-dimensional spatial Fourier transform of the monochromatic wavefront with a corresponding portion of the second optical system to receive the DC component of the two-dimensional spatial Fourier transform of the monochromatic wavefront.

3. The optical system of claim 1, further comprises post processing circuitry connected the detector to receive the data corresponding to the detected interference pattern, the post processing circuitry configured to determine a peak in the received data, wherein a peak in the received data corresponds to the DC component being in phase with the non-DC components.

4. The optical system of claim 3, wherein the post processing circuitry comprises a phase-lock loop to determine the peak in the received data.

5. The optical system of claim 1, wherein the third optical system comprises an adjustable optical element, wherein a position of the adjustable optical element is moved to change a path length of the DC component.

6. The optical system of claim 5, wherein movement of the adjustable optical element corresponds to a wavelength of light from the monochromatic wavefront.

7. The optical system of claim 1, further comprises a fifth optical system to receive the non-DC components, the fifth optical system is configured to direct the non-DC components toward the detector.

8. The optical system of claim 1, wherein the second optical system comprises an optical component having a first portion and a second portion, wherein the first portion comprises a transparent material configured to permit the non-DC component to pass through the optical element and the second portion comprises a metallic material configured to reflect the DC component to the third optical system.

9. The optical system of claim 1, wherein the third optical system is positioned to provide a path length for the DC component such that the DC component forms a plane wave prior to reaching the fourth optical system.

10. The optical system of claim 1, wherein the detector comprises a two-dimensional pixel array to capture an image of the interference pattern.

11. An optical system to correct for distortion in a monochromatic wavefront, the optical system comprising:

a first optical system to receive a monochromatic wavefront, the first optical system configured to produce a two-dimensional spatial Fourier transform of the monochromatic wavefront;

a second optical system to receive the two-dimensional spatial Fourier transform of the monochromatic wavefront, the second optical system configured to adjust the phase across the two-dimensional spatial Fourier transform of the monochromatic wavefront to form a corrected Fourier version of the monochromatic wavefront;

a third optical system to receive the corrected Fourier version of the monochromatic wavefront, the third optical system configured to separate the corrected Fourier version of the monochromatic wavefront into a DC component and non-DC components;

a detector configured to detect the non-DC components from the optical system and provide data corresponding to the detected non-DC components; and a controller configured to receive the data corresponding to the detected non-DC components and determine adjustments to the second optical system to correct for distortion in the monochromatic wavefront.

12. The optical system of claim 11, wherein the second optical system comprises a spatial light modulator having an array of adjustable mirrors.

13. The optical system of claim 12, wherein the controller provides instructions to the spatial light modulator to adjust a position of one or more adjustable mirrors of the array of adjustable mirrors to provide phase and alignment adjustments in the corrected Fourier version of the monochromatic wavefront.

14. The optical system of claim 12, wherein the controller is configured to provide an output having an array of numbers representing a position of each adjustable mirror of the plurality of adjustable mirrors.

15. The optical system of claim 11, further comprises an output connection, wherein the DC component from the third optical system is provided to the output connection.

16. The optical system of claim 11, wherein the third optical system comprises an optical component having a first portion and a second portion, wherein the first portion comprises a transparent material configured to permit the non-DC component to pass through the optical element and the second portion comprises a metallic material configured to reflect the DC component.

17. The optical system of claim 11, wherein the controller is configured to determine the distortion in the monochromatic wavefront based on a configuration of the second optical system that corrected the distortion in the monochromatic wavefront.

18. The optical system of claim 11, wherein the controller is configured to provide an output having an array of numbers representing a current state of the second optical system.

19. The optical system of claim 11, wherein the detector comprises a two-dimensional pixel array to capture an image of the non-DC components.

20. The optical system of claim 11, further comprises a fourth optical system to receive the non-DC components, the fourth optical system is configured to direct the non-DC components toward the detector.

* * * * *